Figure 23:
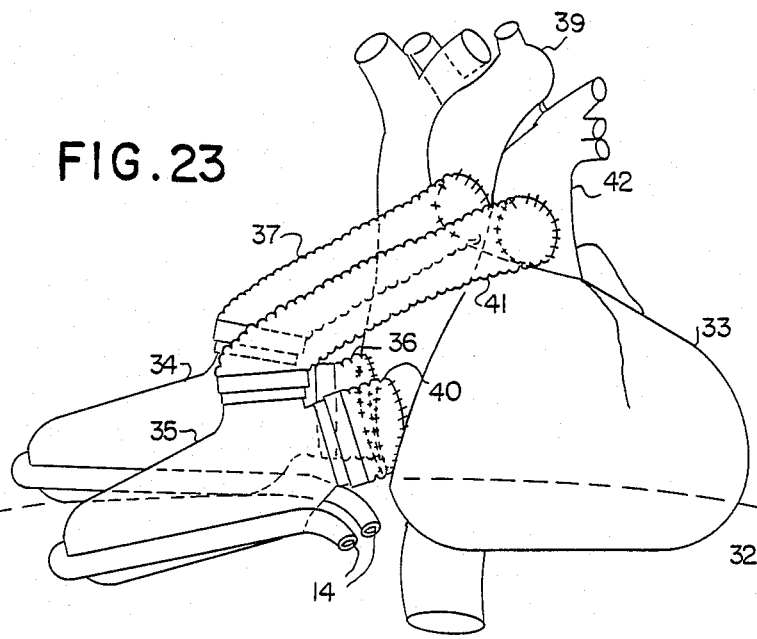

United States Patent [19]

Slonina

[11] Patent Number: 4,851,002
[45] Date of Patent: Jul. 25, 1989

[54] COUPLABLE HEART ASSISTANCE MODULES

[75] Inventor: Jean P. Slonina, Le Vesinet, France

[73] Assignee: Biomasys, Sarl, Le Vesinet, France

[21] Appl. No.: 91,590

[22] Filed: Aug. 31, 1987

[30] Foreign Application Priority Data

Sep. 9, 1986 [FR] France ................................ 86 12592

[51] Int. Cl.$^4$ .............................................. A61F 2/22
[52] U.S. Cl. ...................................................... 623/3
[58] Field of Search ........................... 417/394; 623/3;
128/1 D

[56] References Cited

U.S. PATENT DOCUMENTS

| | | | |
|---|---|---|---|
| 3,062,153 | 11/1962 | Losey | 417/394 |
| 3,641,591 | 2/1972 | Kolff | 623/3 |
| 3,766,567 | 10/1973 | Kahn | 623/3 |
| 4,015,590 | 4/1977 | Normann | 128/1 D |
| 4,051,840 | 10/1977 | Kantromtz | 128/1 D |

FOREIGN PATENT DOCUMENTS

2619239 7/1977 Fed. Rep. of Germany .
2107724 5/1972 France .
270654 1/1928 United Kingdom ................ 417/394

Primary Examiner—Richard J. Apley
Assistant Examiner—James Prizant
Attorney, Agent, or Firm—Roland Plottel

[57] ABSTRACT

The invention provides a prosthesis for mono or biventricular cardiac assistance implanted in the right hemi thorax between the diaphragm and the right lung. The prosthesis of the invention comprises for each module an outer shell (1) of revolution containing a bladder (8) whose shape in the condition expanded by the activation gas is of revolution and coaxial. Two blood orifices (2) and (3) provided with an outlet and inlet valve equip one end of the shell and are connectable by high speed connections to flexible ducts (21) one end of which is sewn to the base of an outlet artery or to an auricle of the defective heart. If two modules are used, they may be equipped with adjustable mechanical coupling means.

The invention may be applied to cardiac assistance under reanimation, possibly for a long period of time.

8 Claims, 7 Drawing Sheets

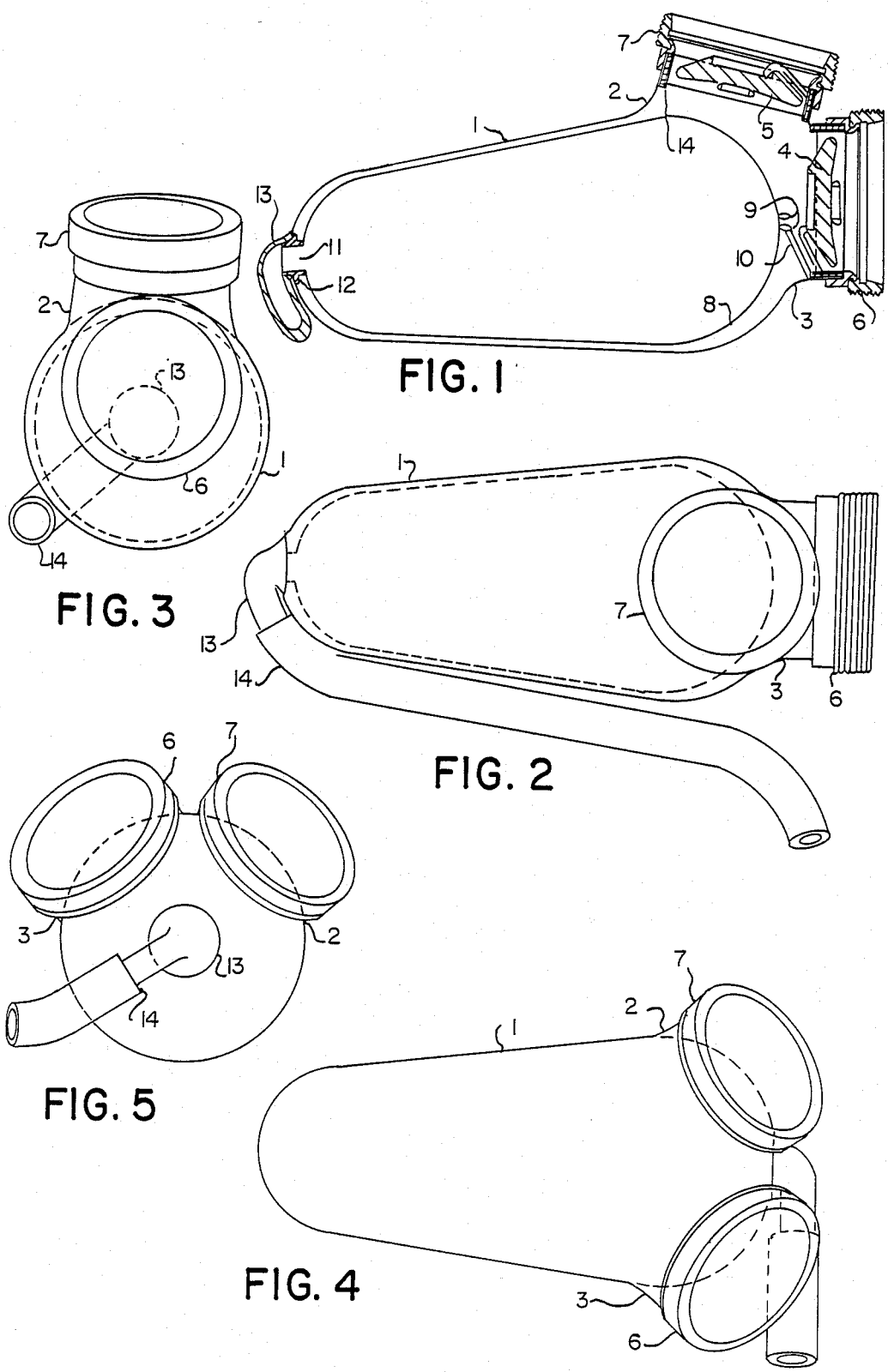

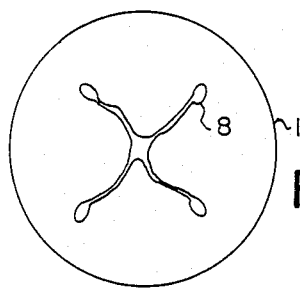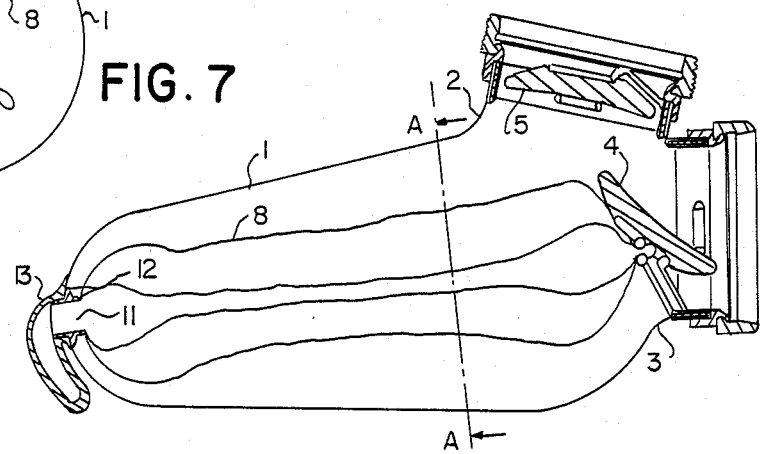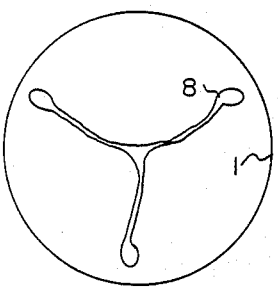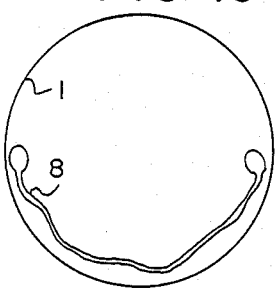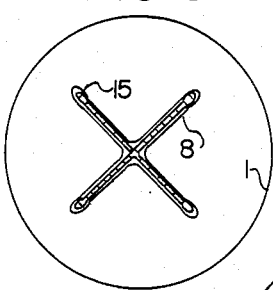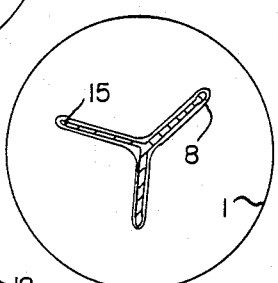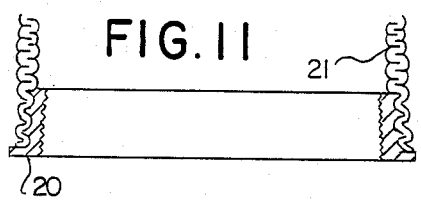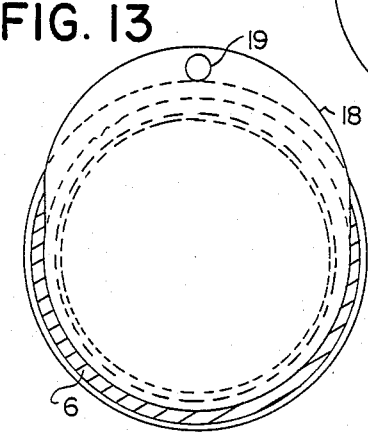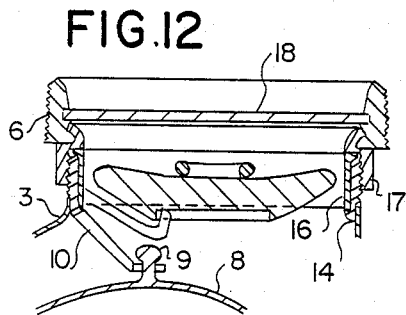

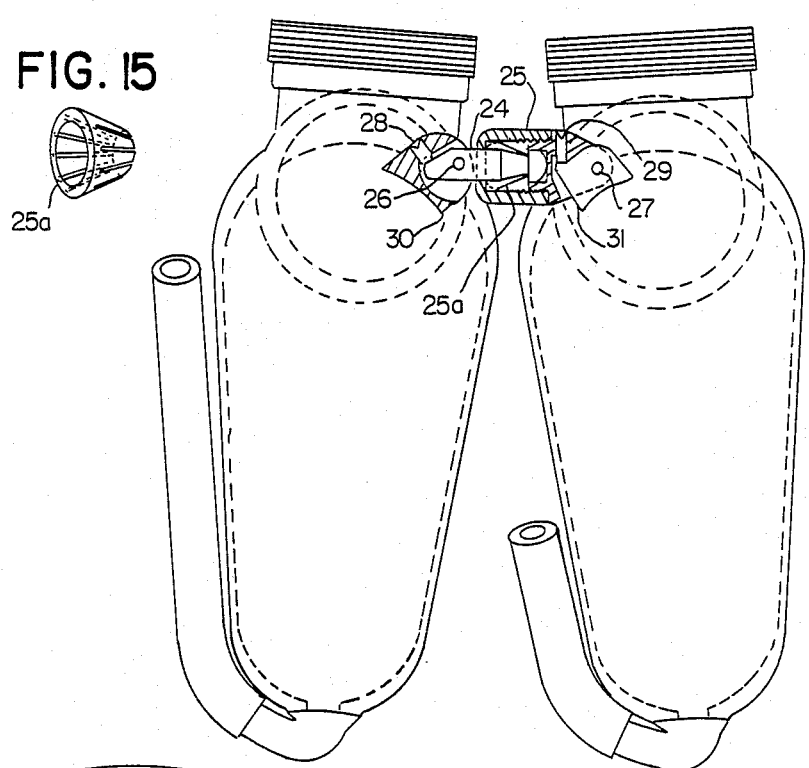
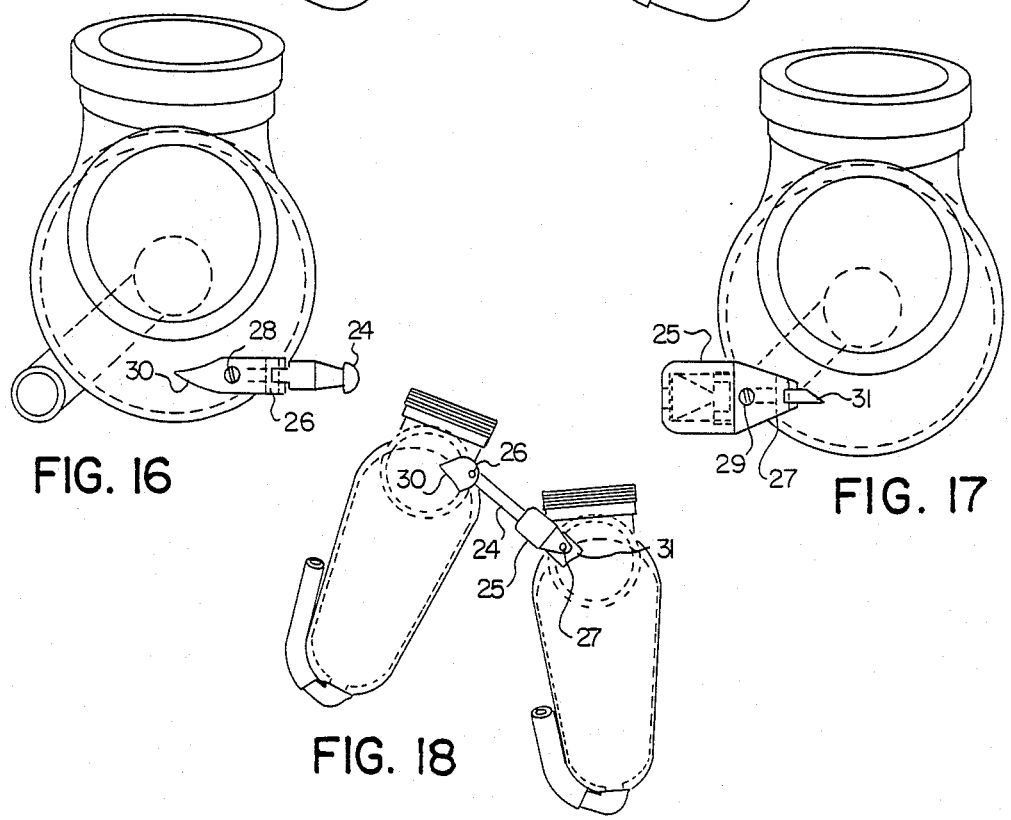

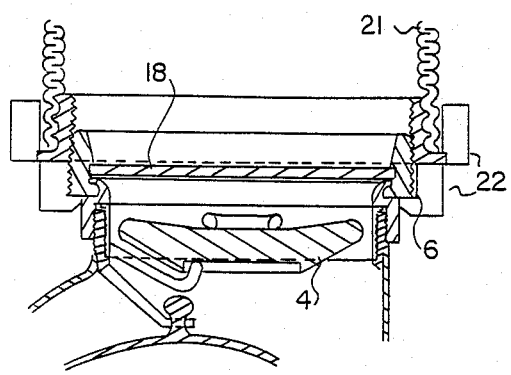
FIG. 19
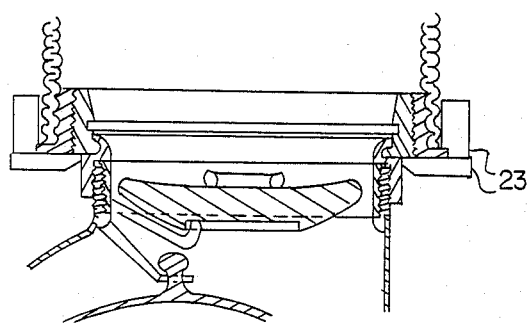
FIG. 20
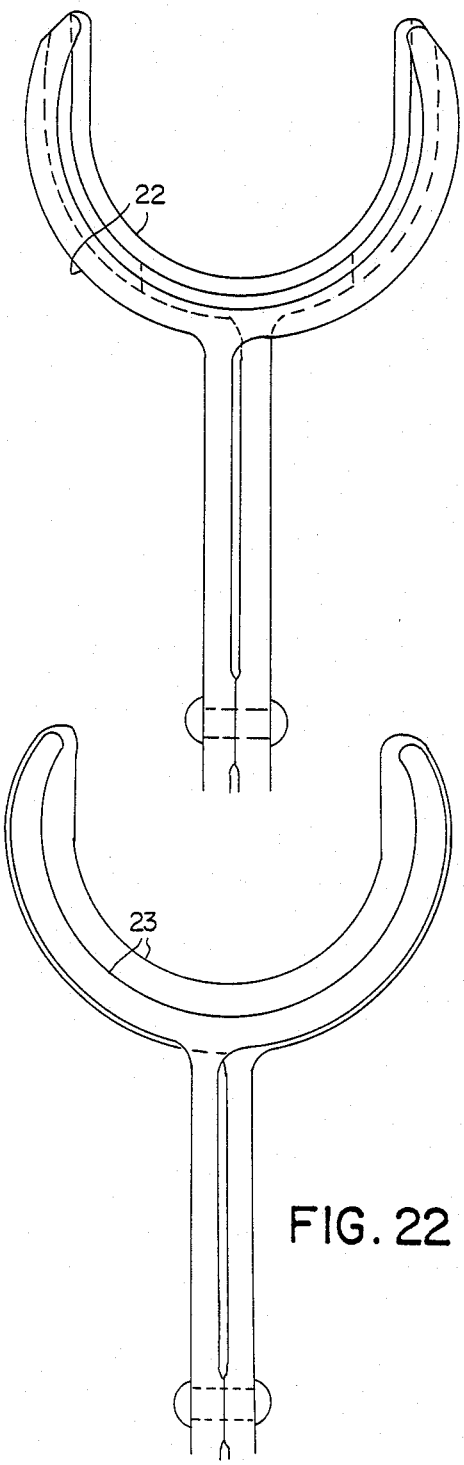
FIG. 21
FIG. 22

COUPLABLE HEART ASSISTANCE MODULES

The present invention relates to the field of reanimation and heart aid equipment.

It consists more precisely in one or two blood pumping modules actuated with a compressed gas, capable of aiding the defective operation of one or two heart ventricles. Each module comprises a membrane pump, a suction orifice having an inlet valve and connected by a flexible duct to a right or left auricle and a delivery orifice having an outlet valve and connected by another flexible duct to the pulmonary artery or to the aorta.

Present heart surgery has numerous applications for such a system, among which:
Patients with acute cardiac insufficiency who must be helped immediately in the uncertain wait for a natural heart doner,
Patients having just undergone an operation requiring stopping of the heart and in whom this organ starts up again in an unsatisfactory way.

The technological background is so far as heart pumps are concerned is now fairly wide. We may mention the following defects:
poor respect of the physiology
mechanical reliability
frequent hemolysis and thrombosis
discomfort for the patient
difficulty of use for the surgeon.

The prosthesis of the invention aims at reducing all these drawbacks.

When the need suddenly appears of mechanically assisting the pumping capacity of a heart momentarily or definitively defective, the tool used must be able to face up to different requirements among which:
the size of the pumpable volume required for each ventricle depending on the gravity of the case,
the geometrical dimensions of the rib cage where the operation is to take place,
the foreseeable operating time of the prosthesis,
the habits or preferences of the surgeon for the sites of connecting the prosthesis to the heart of the patient which may be further influences by the clinical case considered.

For these reasons, it is preferable to use separate pumping modules but if desired they may be connected mechanically together at the optimum distance and in the position and with the most appropriate mutual degrees of freedom.

With separate modules, the optimum pumping volume may be chosen for each ventricle, this volume being zero in some cases especially if the apparatus is to be used for only a relatively short time. There is then only one module which is simpler and more rapid to position, this factor being possibly of a prime importance.

Because of the very great simplicity of the modules of the invention and because of the low cost price which results therefrom, it is possible for an operating block to permanently have an extensive range thereof, for the dimensions and variety of types of connection for which they must be suitable.

Since the patient benefits in all cases from the smallest possible prosthesis, he is subjected to a minimum discomfort. Furthermore, this perfect adaptability, associated with the fact that the modules are generally positioned between the diaphragm and the right lung complies to a maximum with the physiology.

The operation of the membrane pump of revolution, concentric and internal to the hemocompatible envelope gives the best guarantees for the absence of hemolysis and thrombosis. On the one hand, this principle perfectly guarantees the absence of local over pressures and shearing of the blood ending in hemolysis since the radius of the membrane is always less than the local internal radius of the envelope. On the other hand, the internal flow of the blood during filling and ejection is very easy, which avoids thrombosis and leads to very reduced pressure losses.

Finally, this principle allows very accurate control for the bladder of revolution readily withstands a gas over pressure at the end of blood injection without risking jamming of this latter between walls of the envelope. The compressed gas generator sees then a sudden over pressure peak appear which serves as signal for stopping pumping.

The more expansive the bladder, the less sudden is this peak but it remains generally sufficiently sharp.

Another advantage of this prosthesis is its reliability. Since the bladder of revolution has no crimping with concentrations of forces and since furthermore it does not slide over any other surface, it then undergoes no fatigue. Moreover, because of the simplicity of assembly of the internal components an envelope may be used without welding or bonding except at the junction with the valves and with the gas pipe.

The prosthesis of the invention comprises then, for each module, first of all an external shell of revolution. This shell is preferably elongate along it axis and is conical so as to promote introduction under the right lung but this is not limitative. It could also for example be cylindrical and elongate, or cylindrical or conical but very little elongated. Each of the ends with respect to the axis of revolution has preferably a substantially hemispherical shape. One of the two ends, generally the largest, has the inlet and outlet orifices each fitted with a valve. Although some usual examples or arrangements are given in the illustration, the exact position of the inlet and outlet orifices on said end is not limitative of the invention.

The material forming the very thin shell may be a biocompatible metal formed for example by electrode deposition, or any metal coated with a biocompatible protective layer such as carbon or a chromium-cobalt alloy. It may also be a biocompatible plastic material formed by any known method. In all cases, the shell, after formation, is coated on the inside with a hemocompatible material such for example as polyurethane.

Inside the shell is situated a flexible bladder of revolution which is the blood pumping member. The material which forms it or at least which covers it is necessarily hemocompatible, such for example as polyurethane. The general shape of the inflated bladder is very close to that of the envelope but its dimensions even under maximum expansion are always slightly less than those of the inside of the envelope so as to avoid jamming of the blood. The bladder is adapted to be folded completely under the effect of an internal compression, while leaving practically only the volume of the material which forms it as residual volume. The ratio between the pumpable volume and the total outer volume of the prosthesis is therefore very little removed from one, which is very favorable for the patient.

The gas supply for the bladder is provided axially through one of its ends. For some arrangements of the blood orifices, either of the two ends may be chosen whereas for other arrangements the gas supply is necessarily provided from the side opposite the blood orifices.

The axial end of the bladder which is opposite the gas intake preferably has an anchorage point which positions it on the geometrical axis of the envelope but this is not obligatory in accordance with the invention.

The bladder is formed in a mold or on an internal meltable support whose section resembles the shape of a star with three or four arms so as to have an influence on the shape which it assumed in the folded state under the effect of a depression. The aim is to regularize the blood flows about the axis so as to avoid the risks of thrombosis.

Another solution for regularizing the blood flows is that the bladder contains a rigid or semi rigid internal framework, made from elastomer for example, which guides folding thereof under the effect of the depression. However, these improvements are not limitative to the invention.

The bladder may possibly comprise an inextensible framework, made from a fabric embedded in the polyurethane for example so as to increase the sharpness of the gas overpressure signal at the end of expansion of the blood.

When two modules are used for the same patient, it is possible, depending on the circumstances and the scheduled duration of the implantation to couple them mechanically together. This is however not obligatory and the modules are not necessarily provided with coupling means.

The effect of coupling is to hold the two modules at the desired distance and in the desired relative position depending on the size of the modules and the type of implantation and connection to the heart chosen by the surgeon. With such mutual positioning, the assemlby of the two modules may occupy a stable position with respect to the heart and to the anterior and/or posterior limits of the rib case. It also means that they do not clash. On the other hand, coupling which is too rigid is incompatible with the high deformability of the diaphragm, which may be the source of high stresses in the flexible connections to the heart. It is therefore useful to have coupling keeping certain degrees of freedom.

The method of coupling of the invention which in no wise limits the scope thereof is a mechanical connection which connects together the ends carrying the blood connection orifices of two modules. Because of the position of this connection, it is possible to keep relative degrees of freedom without that resulting in dangerous over stresses for the ducts sewn to the heart.

The coupling essentially comprises a mean connection formed of a male part and a female part, axially fitted together and locked in the same gesture by means of a conical spring and allowing axial rotation of the male part in the female part.

The main connection is connected to each module by means of an articulation with axis perpendicular to that of the main connection and of the module concerned. An adjustable screw limits the angular movement of the main connection in the articulation integral with each module.

So as to be able to adjust the spacing of the module at their orifice carrying end, the male part of the main connection is interchangeable with parts of various lengths operating in the same way with the female part.

More considly, the invention is a prosthesis for mono or bi-ventricular heart assistance, implantable in general in the right hemi-thorax, between the diaphragm and the right lung, formed of one or two modules each comprising a membrane blood pump actuated with a compressed gas, having two blood connection orifices connected by flexible ducts, one to the right or left auricle, the other to the pulmonary artery or aorta, each of the orifices being provided with an inlet or outlet valve, this prosthesis being characterized in that:

the external shell of each module has a form of revolution, generally conical with two substantially hemispherical ends, the largest of these ends comprising the two blood connection orifices.

the blood pump is formed by the inside of said shell coated with a hemocompatible material and by a bladder coaxial with the shell, flexible and made from a hemocompatible material, which, when it is subjected to the maximum internal gas pressure, has a shape of revolution close to that of said shell with also two substantially hemispherical ends and whose external dimensions are in all points slightly less than the corresponding internal dimensions of the shell so as not to cause any phenomenon of hemolysis at the end of blood ejection.

in the case of using two modules, they may be equipped with adjustable mechanical coupling means so that they keep the distance, the relative position and the degree of freedom desired.

The invention will be better understood from the following detailed description with reference to the accompanying figures which show:

FIG. 1: an apparatus of the invention, in longitudinal section through its axis and the centers of the two blood connections, the bladder of revolution being in the inflated condition.

FIG. 2: an apparatus in accordance with the invention in an external top view with respect to FIG. 1.

FIG. 3: the apparatus of the invention in an external right hand view with respect to FIG. 1.

FIG. 4: the apparatus in accordance with the invention equipped with the second method of arranging the blood connections in an external view.

FIG. 5: the apparatus of the invention in a right hand external view with respect to FIG. 4.

FIG. 6: an axial section of the apparatus of the invention corresponding to FIG. 1 but with the bladder deflated and the blood intake valve open.

FIG. 7: a section of FIG. 6 through the axis AA showing the external shell and a first form of the section of the deflated bladder.

FIG. 8: a section similar to the preceding one showing a second form of the section of the deflated bladder.

FIGS. 9 and 9A: section similar to the preceding one showing the deflated bladder disposed about the framework.

FIG. 10: a section similar to the preceding one showing a third form of the deflated bladder.

FIG. 11: an axial section of a flexible blood connection duct sewable to the heart, ending in a rigid female connection.

FIG. 12: an axial section of a blood connection orifice comprising an intake valve, a male connection and closure plate.

FIG. 13: an axial view of the orifice shown in FIG. 12 through a sectional plane passing through the closure plate.

FIG. 14: a bottom view of two modules coupled by means of the device shown only in axial section.

FIG. 15: a view of the locking spring of the coupling device.

FIG. 16: an external view from the end carrying the blood connections of a module having the male part of the coupling device.

FIG. 17: an external view similar to FIG. 16 of the module having the female part of the coupling device.

FIG. 18: an external bottom view of two modules coupled together by means of a coupling device whose male part is extended.

FIG. 19: an axial sectional view of a blood connection orifice in which the rigid female connection has been prefitted by means of the tool of which the four nose traces may be seen.

FIG. 20: a view identical to FIG. 19, with the rigid female connection being completely fitted using the tool whose four noses can be seen.

FIG. 21: a top view of the noses of the tool used for the assembly shown in FIG. 19.

FIG. 22: a top view of the noses of the tool used for the assembly shown in FIG. 20.

FIG. 23: a general view, from the front with respect to the individual assumed standing of the natural heart and two modules of the invention, which are connected thereto by a first method of blood connection.

Figure 24:
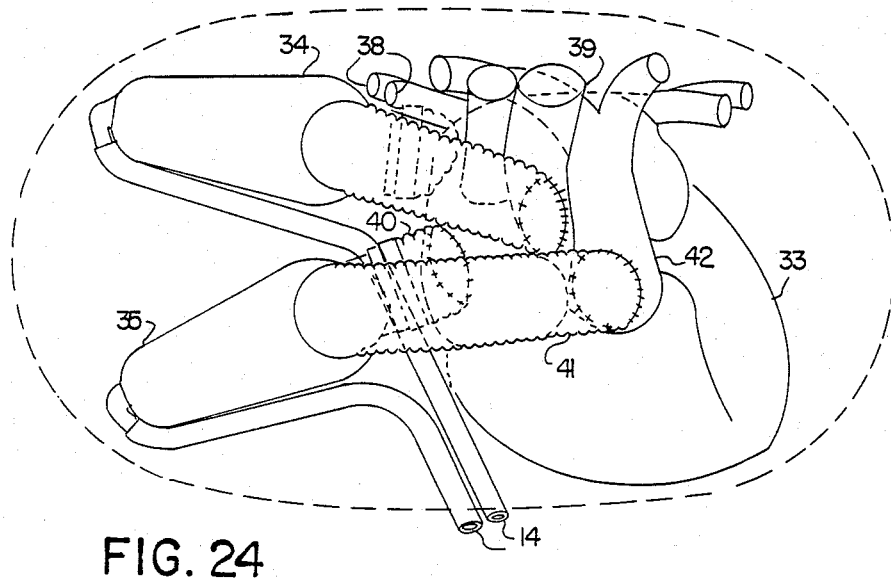

FIG. 24: view of the components of FIG. 23 from the top of the individual assumed standing.

Figure 25:
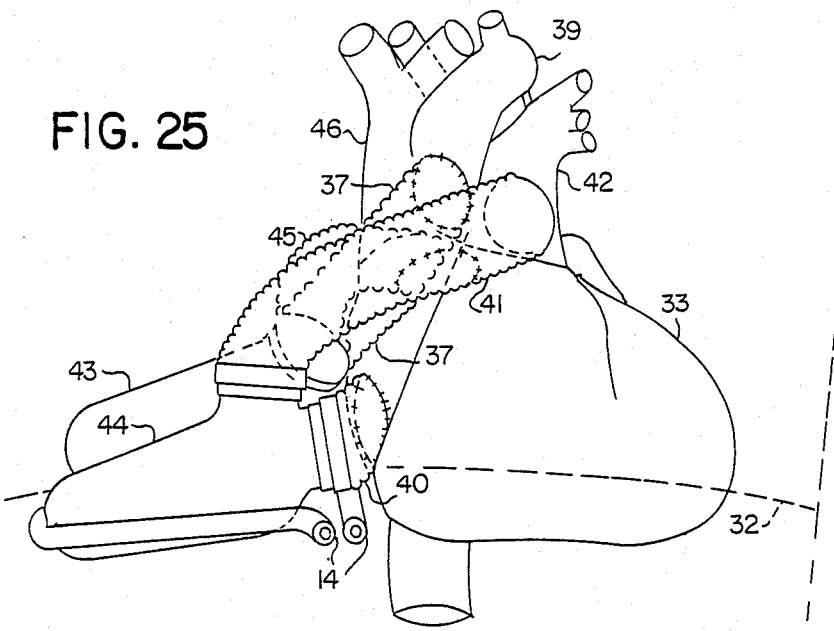

FIG. 25: a general view identical to FIG. 23 but relative to the second method of blood connection.

Figure 26:
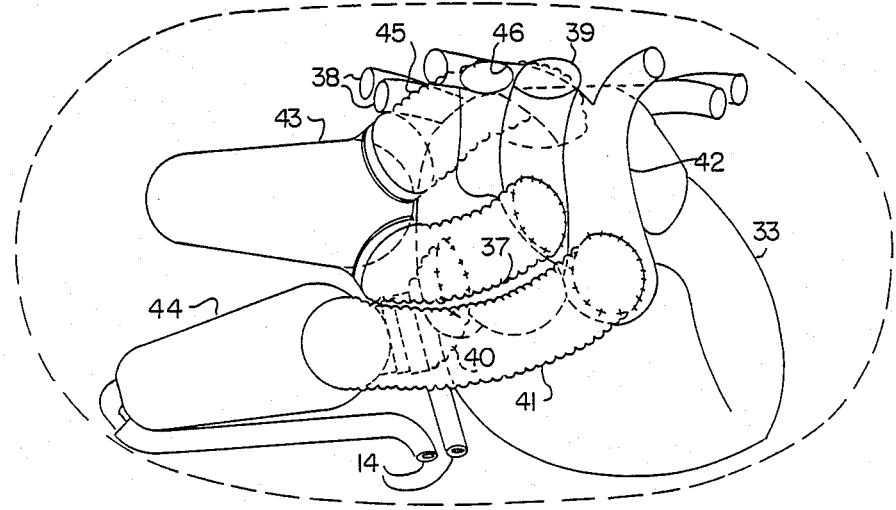

FIG. 26: a view of the components of FIG. 25, from the top of the individual assumed standing.

Figure 27:
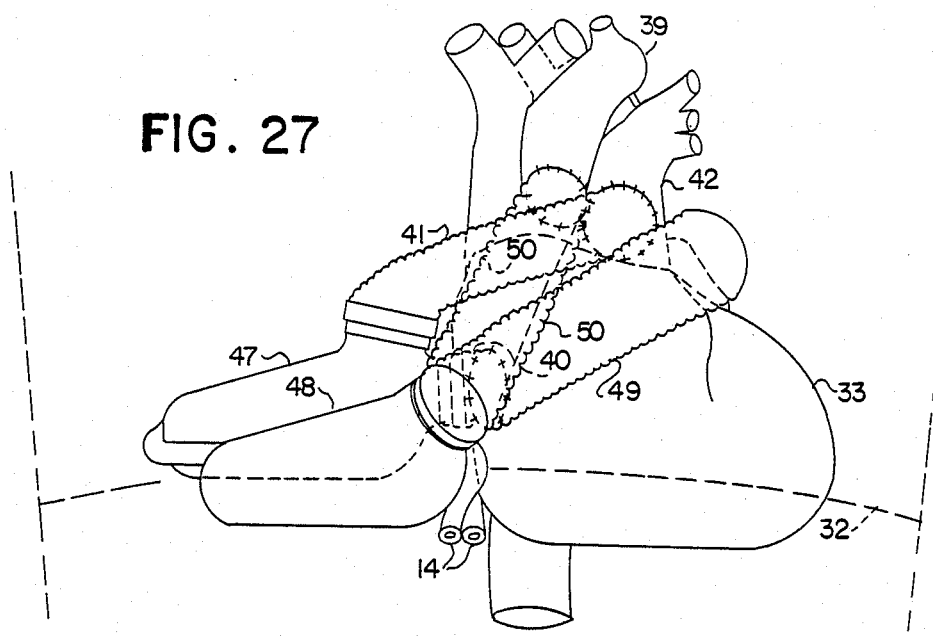

FIG. 27: a general view, identical to FIG. 23, but relative to a third embodiment of blood connections.

Figure 28:
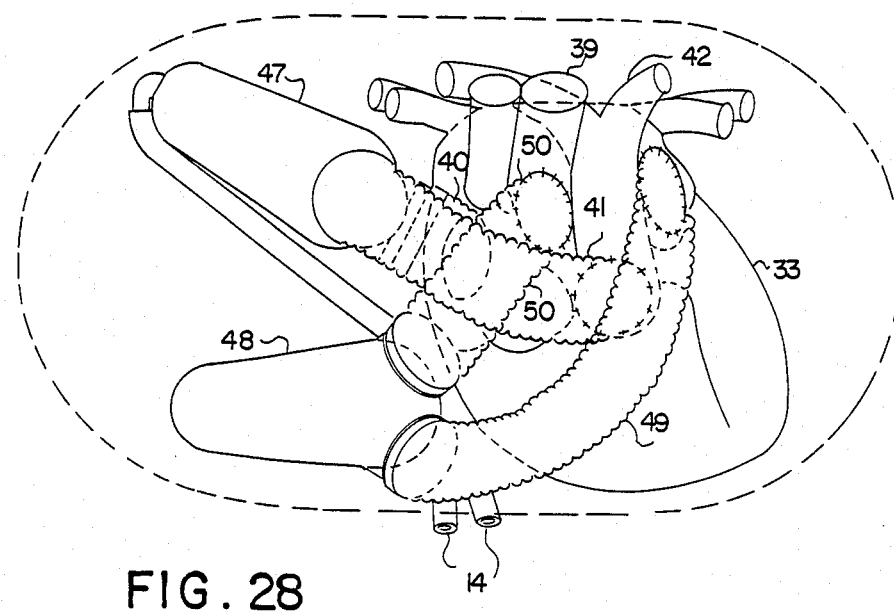

FIG. 28: a view of the components of FIG. 27, from the top of the individual assumed standing.

In FIG. 1 can be seen that external shell 1 which comprises two bosses 2 and 3 for supporting the inlet 4 and outlet 5 valves and the male blood connections 6 and 7. Bosses 2 and 3 are always disposed at the same hemispherical end of the shell but with several possible variants such for example as the one shown in FIGS. 4 and 5.

Inside the shell can be seen the bladder of revolution 8 coaxial with the shell when it is inflated as shown in FIG. 1. This bladder 8 comprises two hemispherical ends one of which is provided with an anchorage point 9 for cooperating with an anchorage piece 10 integral with the shell.

The anchorage point 9 is not necessarily exactly on the axis of bladder 8. Since it cooperates with piece 10 it is only important for it to impose the coaxial position of the bladder under the envelope.

Furthermore, this anchorage point 9 is not limitative of the invention which may possibly not comprise it.

At the other end of the bladder and substantially on the axis thereof, while maintaining an excellent coaxial position of the shell and of the bladder, is to be found that orifice 11 for the intake and withdrawal of inflation gas.

Orifice 11 is provided with a rigid or semi rigid end piece 12 which passes through shell 1 and is assembled by bonding to the connection head 13 of the flexible gas supply tube 14. Head 13 is bonded both to the end piece 12 and to the shell 1.

The shell 1 may be formed by electrodeposition of biocompatible metal on a fusible electrode, or by distamping and welding, or by injection of different biocompatible plastic materials, etc. Piece 10 may be made from metal, hemocompatible and welded for example to the base 14 of a valve. Head 13 may be made from an injected plastic material for example. The bladder and the connections will be discussed further on.

It can be seen in FIGS. 1 to 5 that, depending on the position of bosses 2 and 3 which serves as support for the valves and connections it is possible or not to provide the gas supply through the end of the shell which supports them.

Thus, in the case of FIGS. 1 to 3, the gas supply can only be placed through the end of the shell opposite that which supports the bosses 2 and 3.

On the contrary, in the case of FIGS. 4 and 5, the gas supply may take place through one or other of the two ends.

FIG. 6 is an axial section of a module identical to that of FIG. 1 showing the position of the valves and of the bladder at the beginning of blood intake.

Valve 4 is open, bladder 8 is completely deflated and its shape can be seen in FIG. 7 which is a section through AA. This shape is in this case cruciform. The aim is to avoid having blood volumes which are not renewed as might occur with a folded shape of the bladder such as that shown in FIG. 10.

The arrangement of FIG. 10 may very well operate without problems of thrombosis but those of FIG. 7 and 8 simply provide better security. All the star shaped geometries with "n" arms or that of FIG. 10 form nevertheless a part of the invention.

In order to obtain star shaped folding, two methods may be used:
either forming the bladder, by steeping, blowing, injection, etc. with a mold or a model which prefigures the desired polygonal shape so that, starting with the circular shape expanded of the folding by its own stiffness.

or equipping the bladder with a permanent internal framework 15, rigid or preferably semi rigid, made from elastomer for example.

The bladder is made from a hemocompatible elastomer such as polyurethane for example, It may possibly comprise, particularly in its geometrically developable zones (cone or cylinder), a flexible framework made from a fabric so as to make it practically inextensible.

In FIG. 12 is shown one method of forming an inlet blood orifice having a valve 4, a drain plate and the male part 6 of a high speed connection. This description is in no wise limitative of the invention which may adapted to any type of commercial valve or connection.

The valve base 14 may be seen which is welded to the boss 3 and shell 1. The piece 10 for anchoring the bladder 8 by an anchorage point 9 is welded to the valve base 14.

The external cylindical structure 16 of the valve is freely fitted into the base 14 and is secured by screwing the pivoting piece 17 which allows free rotation of the male part 6 of the high speed connection. This male part 6 includes an opening and a semi circular groove for the lateral sliding of a closure plate 18 also shown in FIG. 13.

FIG. 11 shows the rigid female part 20 of the high speed connection which is to cooperate with the male part 6. A flexible dacron duct 21 for example is fixed in the circular grooves of the female part 20.

The connection operation takes place in two stages after having fitted a module in its position, and after sewing all the flexible ducts 21 to the heart or to its outlet arteries.

In the first stage the female part 20 is fitted, using a first tool 22 shown in FIGS. 19 and 21, on the male part 6 as far as the limit of the closure plate 18. The module has been previously filled with blood or a physiological serum, failing which it will be very difficult to eliminate the bubbles. Then the air contained in the flexible duct 21 is drained, which is easily done and plate 18 has therefore liquid on its two walls.

In the second stage, plate 18 is rapidly removed by means of a hook which is engaged in hole 19 and almost simultaneously the female part 20 is fitted as far as it will go on the male part 6 so as to close the opening which plate 18 occupied. For that, the second tool 23 shown in FIGS. 20 and 22 is used. The connection is then no longer dismountable but its angular orientation may be completed by rotating the male part 6 on the pivoting piece 17.

All the parts forming the valve connections and supports are generally made from hemocompatible metal such as titanium or stainless steel but plastic materials may also be used such as lexan for example.

In FIGS. 14 to 18 are shown the principles of coupling together two modules. These principles are not limitative of the invention but form one possibility thereof. The aim is to complete the holding in position of a module if it is preferred not to leave it subject only to the relatively uncertain positioning provided by its flexible connections with the heart.

For that, an assembly is formed with the other module which may bear on the limits of the rib cage. It is then necessary, as can be seen in FIG. 18, for the modules to be able to adopt relative very particular positions depending on the case concerned.

Certain degree of freedom must also be kept so that deformation of the diaphragm does not lead to an accidently high stress on the sewing which connects the flexible ducts 21 to the heart or to its arteries.

The coupling must finally be provided close to the ends of the shells which are provided with connections, so that an appreciable movement of the other end of the module does not induce a small movement at the connections.

In FIG. 14 can be seen the axial section of a coupling system.

It comprises the male part 24 of the main connection and the female part 25. The female part 25 comprises on the inside a conical perforated blade spring 25a shown in FIG. 15.

Because of this spring which serves as pawl which engages in a circular cuspate groove of the male part 24, the male part 24 may be fitted axially in the female part 25 but it cannot be withdrawn unless the female part 25 is unscrewed. After such fitting together, the male and female parts may rotate axially one in the other, which produces one degree of freedom between the two modules. If for any reason this degree of freedom is not desirable, it is sufficient for the male and female parts to have a cooperating but non circular external and internal section.

The main connection formed of parts 24 and 25 is connected to the two modules by an articulation 26 and 27 whose axis is perpendicular to the axis of 24 and 25 and substantially perpendicular to the axis of the module.

These axes 26 and 27 allow the relative positions of the two modules to be obtained. These positions are then maintained by means of screws 28 and 29 shown in FIGS. 14, 16, 17. It can be seen that the articulations 26 and 27 are only limited in one direction which is sufficient for the modules cannot move outwardly apart, since they are limited by the rib cage. The articulations 26 and 27 and screws 28 and 29 are carried by pieces 30 and 31 integral with the shell of the modules.

In FIGS. 23 and 24 a first method can be seen of implanting the modules with respect to the thorax and particularly with respect to the forwardly slanted diaphragm 32 and the heart 33.

Module 34, of a type similar to that of FIGS. 1, 2 and 3, assists the left ventricle and module 35 of a type identical but of a smaller size in general assists the right ventricle.

The flexible suction 36 and delivery 37 ducts of module 34 are sewn respectively to the left auricle between the right pulmonary veins 38 and the right auricle and to the base of the aorta 39.

The flexible suction 40 and delivery 41 ducts of module 35 are therefore connected respectively to the right auricle and to the base of the pulumonary artery 42.

In FIGS. 25 and 26, a second method can be seen of implanting modules with respect to the thorax.

Module 43 of a type similar to that of FIGS. 4 and 5 assists the left ventricle and module 44 of a type similar to that of FIGS. 1, 2 and 3 assists the right ventricle exactly as in the preceding case.

The flexible delivery duct 37 of module 43 is still sewn to the base of the aorta 39 but the flexible suction duct 45 reaches the left auricle to which it is sewn while passing round the right pulmonary veins 38 over the top so as to be able to form a wider connection than in the preceding case for its concerns the top of the left auricle.

The passage of the flexible duct 35 cannot adversely effect the current of the venous return from the upper vena cava 46 for the pressure which reigns there is also a venous pressure.

In FIGS. 27 and 28 a third method can be seen of implanting modules with respect to the thorax.

Module 47, placed behind and of a type similar to that of FIGS. 1, 2 and 3 this time assists the right ventricle and its flexible connection ducts 40 and 41 are sewn respectively to the right auricle and to the base of the pulmonary artery 42.

Module 48 placed in front and of a type similar to that of FIGS. 4 and 5 assists the left ventricle and its flexible suction 49 and delivery 50 ducts are connected respectively to the top of the left auricle while passing round the pulmonary artery 42 and to the base of the aorta 39 while passing under duct 41.

Of course, these three methods of implantation are only given by way of example so as to show the very great flexibility of use of the modules of the invention. The choice of each type of implantation in fact depends solely on the opinion of the surgeon as a function of the clinical case concerned.

The gas supply for the prosthesis does not belong to the field of the invention. It may be provided by a compressor integrated in the body or external thereto. In this case, the flexible tubes 14 pass through the thoracic or abdominal wall by means of a known system for avoiding the passage of microbes. The heart prosthesis of the invention is controlled, regulated and slaved by a known control system. The general principle is the slaving of the heart beat to the venous return pressure, the role of the heart being, physiologically, to drive the blood which is receives and not to provide for the needs for the organism. The slaving system also determines more particular the two thirds/one third distribution of the diastole and systole times and detects the increase of gas pressure corresponding to the end of the systole. All these functions are taken into account by the compressed gas generation apparatus at present available for heart prostheses.

Of course, the invention is in no way limited to the embodiment described and shown and comprises all the technical equivalents of the means described as well as combinations thereof if they are carried out in the spirit of the invention and used within the scope of the following claims.

I claim:

1. A prosthesis for mono or biventricular cardiac systems, generally implantable in the right hemithorax, between the diaphragm and the right lung formed of one or two modules each comprising a membrane blood pump actuated with a compressed gas, having two blood connection orifices connectable by flexible ducts, one to the right or left auricle, the other to the pulmonary artery or the aorta, each of the orifices being provided with an inlet or outlet valve, this prosthesis being characterized in that:

the outer shell of each module has a form of revolution, generally conical with two substantially hemispherical ends, the largest of these ends comprising the two blood connection orifices;

the blood pump is formed by the inside of said shell coated with a hemocompatible material and by a flexible bladder coaxial with the shell, made from a hemocompatible material, which, when it is subjected to the maximum internal gas pressure, has form of revolution close to that of said shell with also two substantially hemispherical ends and the external dimensions of which are in all points slightly less than the corresponding inner dimensions of the shell so as not to cause any hemolysis phenomenon at the end of blood ejection; wherein the bladder has a coaxial rigid or semirigid internal framework whose section is that of a star with three or four arms so as to avoid problems of thrombosis between the bladder and the shell.

2. The prosthesis according to claim 1, characterized in that the bladder (8) is supplied with compressed gas through an orifice (11) disposed substantially on the axis thereof.

3. The prosthesis according to claims 1 or 2, characterized in that the bladder (8) has an anchorage point (9) situated substantially axially on the end opposite that which comprises the gas supply (11) and cooperating with an anchorage piece (10) integral with the shell (1) whose role is to maintain the bladder (8) perfectly coaxial with the shell (1).

4. The prosthesis according to claims 1 or 2, characterized in that the flexible hemocompatible elastomer bladder has has a flexible fibrous framework which when normally inflated is not further extendible.

5. The prosthesis according to claims 1 or 2, characterized in that, in the case of using two modules, they are coupled by means of a male part (24) integral with one module which, after all the blood connection operations have been carried out, is fitted for a single translational axial movement in a female part (25); said female part being integral with the other module; the female part (25) having a conical blade spring (25a) whose blades engage in a step of the male piece (24); wherein with this coupling, a mutual movement of rotation about the axis of parts (24) and (25) is preserved between the two modules (FIG. 8).

6. The prosthesis according to claim 5, characterized in that the male part (24) may have different lengths.

7. The prosthesis according to claim 5, characterized in that the male (24) and female (25) parts are fixed to the module of which they form part, respectively by means of articulations (26) and (27) having an axis substantially perpendicular to their own axis and to the axis of the module.

8. The prosthesis according to claim 5, characterized in that the angular free movement of the articulations (26) and (27) is limited in one direction by means of an adjustment screw (28) and (29) respectively.

* * * * *